United States Patent [19]

Ballantine et al.

[11] Patent Number: 4,605,806

[45] Date of Patent: Aug. 12, 1986

[54] PROTON-CATALYZED REACTIONS CATALYZED BY HYDROGEN ION-EXCHANGED LAYERED CLAYS

[75] Inventors: James A. Ballantine, West Cross, Wales; Reginald Gregory, Camberley, England; John H. Purnell, Bishopston, Wales; John M. Thomas, Cambridge; David J. Westlake, Woking, both of England

[73] Assignee: The British Petroleum Company p.l.c., London, England

[21] Appl. No.: 697,510

[22] Filed: Feb. 1, 1985

Related U.S. Application Data

[60] Division of Ser. No. 417,873, Sep. 14, 1982, abandoned, which is a continuation-in-part of Ser. No. 218,552, Dec. 22, 1980, abandoned.

[30] Foreign Application Priority Data

| Dec. 22, 1979 | [GB] | United Kingdom | 7944315 |
| May 17, 1980 | [GB] | United Kingdom | 8016384 |
| Jul. 5, 1980 | [GB] | United Kingdom | 8022102 |
| Jul. 5, 1980 | [GB] | United Kingdom | 8022101 |
| Aug. 9, 1980 | [GB] | United Kingdom | 8026028 |

[51] Int. Cl.$^4$ ............................................. C07C 2/68
[52] U.S. Cl. ................................... 585/467; 585/468
[58] Field of Search ........................ 585/467, 468

[56] References Cited

U.S. PATENT DOCUMENTS

| 2,384,505 | 9/1945 | Thomas et al. | 585/468 |
| 3,204,005 | 8/1965 | Nixon | 585/467 |
| 3,268,607 | 8/1966 | Schmitt et al. | 585/468 |
| 4,238,364 | 9/1980 | Shabtai | 502/65 |
| 4,499,319 | 2/1985 | Ballantine et al. | 585/467 |

Primary Examiner—Curtis R. Davis
Attorney, Agent, or Firm—Brooks Haidt Haffner & Delahunty

[57] ABSTRACT

The invention relates to the use of hydrogen ion-exchanged layered clays in organic reactions which are catalyzed by protons. Such organic reactions include the production of ethers by the reaction of an alcohol with an olefin or an olefin oxide, the production of an ether by the reaction of a primary or secondary aliphatic alcohol or an olefin oxide, the production of an alkyl aromatic compound by the reaction of an aromatic hydrocarbon with an olefin or a $C_2$ or higher alcohol and the production of an alcohol by the hydration of an olefin.

11 Claims, No Drawings

PROTON-CATALYZED REACTIONS CATALYZED BY HYDROGEN ION-EXCHANGED LAYERED CLAYS

This is a division, of application Ser. No. 417,873, filed Sept. 14, 1982, which is a continuation-in-part application of pending prior application Ser. No. 218,552, filed Dec. 22, 1980, both now abandoned.

The present invention relates generally to proton-catalysed organic reactions and in particular to the use of hydrogen ion-exchanged layered clays as catalysts in organic reactions catalysed by protons.

Many different types of organic reaction are catalysed by protons or, to give them another name, hydrogen ions. Typical of such reactions are olefin hydration in which the product is an alcohol, esterification of an alcohol with an acid in which the product is an ester and the decomposition of organic hydroperoxides, e.g. cumene hydroperoxide in which the products are phenol and acetone. Generally the protons are provided by the dissociation of a strong mineral acid or a strong organic acid. Thus sulphuric acid and para-toluene sulphonic acid have been used extensively as catalysts in the industrial production of esters, and phosphoric acid, usually supported on silica, is a catalyst commonly employed in the commercial production of ethanol. Comparatively recently hydrogen ion-exchanged resins have been employed as catalysts in, for example, the production of alkanols.

In the Journal of Physical Chemistry, Volume 44, No. 2, February, 1940, pp 180 to 184, there is disclosed the preparation of an acid bentonite by electrodialyzing a 4 percent suspension of Wyoming bentonite in a cell of the Mattson type until the catholyte liquor is no longer alkaline and the use of the acid bentonite so-prepared as catalyst in the decomposition of hydrogen peroxide.

It is also known from the complete specification of British Pat. No. 905,854 to produce tertiary butyl acetate by reacting isobutene with acetic acid at a temperature within the range 0° to 100° C. in the presence of an acid-activated silicate, which may be a Fullers earth, montmorillonite, bleaching earth, clay or kaolin activated by treatment with mineral acid. U.S. Pat. No. 4,278,820 describes a process for producing a monoalkylene glycol monoether by reacting an alkylene oxide having 2 to 4 carbon atoms with an aliphatic alcohol having 1 to 4 carbon atoms in which the improvement comprises performing the reaction in the presence of a solid catalyst resulting from the exchanging of exchangeable cations of a clay composed mainly of montmorillonite with at least one cation selected from the group consisting of aluminium, chromium, manganese, iron, tin and thorium. There is no disclosure in U.S. Pat. No. 4,278,820 of the use of a hydrogen ion-exchanged layered clay. The introduction of U.S. Pat. No. 4,278,820 defines an activated clay as one having enhanced adsorptive characteristics obtained by treating the acid clay with a mineral acid. It is also stated that the activated clay scarcely contains montmorillonite because the montmorillonite structure is broken in the process of acid treatment.

Thereafter in the Journal of Catalysis 58, 238–252 (1979) Adams et al disclosed that metal cation-exchanged water-intercalated clays such as metal cation-exchanged water-intercalated montmorillonites will convert alkenes to the corresponding bis-sec-alkyl ethers. Although the catalytic activity of a variety of metal cation-exchanged clays is described, there is no disclosure of a hydrogen ion-exchanged clay.

We have now found that hydrogen ion-exchanged layered clays catalyse those organic reactions which are catalysed by protons. The hydrogen ion-exchanged layered clays as used in the process of the present invention are to be distinguished from the previously used acid-activated clays in that their layered structure is essentially retained and they do not contain free mineral acid. Compared with naturally occuring clays, the hydrogen ion-exchanged clays have a greater catalytic activity.

Accordingly the present invention provides a process for carrying out a proton-catalysed organic reaction characterised in that there is used as catalyst a hydrogen ion-exchanged layered clay.

A layered clay within the context of the present specification is a clay having a lamellar structure with interlamellar spaces disposed between the lamellar layers. Typical of such clays is montmorillonite which has an idealised stoichiometric composition corresponding to $Na_{0.67}[Al_{3.33}Mg_{0.67}](Si_8)O_{20}(OH)_4$. Structurally it comprises a central layer containing octrahedrally coordinated aluminium and magnesium in the form of their oxides and hydroxides sandwiched between two layers containing tetrahedrally coordinated silicon essentially in the form of its oxide. Normally in nature cations are present to compensate for the charge imbalance caused by isomorphous substitution of $Mg^{2+}$ for $Al^{3+}$ in the octahedral layer, and/or $Al^{3+}$ or other ions for $Si^{4+}$ in the tetrahedral layers. The octahedral and tetrahedral regions are tightly bound together to form a lamellar layer. The space between these lamellar layers, i.e. the interlamellar space, in natural clays is normally occupied by exchangeable $Ca^{2+}$ or $Na^+$ ions. The distance between the interlamellar layers can be substantially increased by absorption of a variety of polar molecules such as water, ethylene glycol, amines etc., which enter the interlamellar space and in doing so push apart the lamellar layers. The interlamellar spaces tend to collapse when the molecules occupying the space are removed, for example by heating the clay at a high temperature. Both natural and synthetic clays having a layered structure are well known and may be used in the process of the invention after exchange of the interlamellar metal cations normally associated therewith with hydrogen ions. Besides montmorillonites such as bentonite and Fullers Earths, other types of suitable clays include hectorites, beidellites, vermiculites and nontronite. Preferably the clay is a bentonite, such as Wyoming bentonite.

Techniques for obtaining a hydrogen ion-exchanged material from a cation exchangeable material are well known and include:

(i) exchange with excess hydrogen ions in solution, customarily an aqueous solution of a mineral acid, and (ii) exchange with an aqueous solution of an ammonium compound to produce the ammonium ion-exchanged material followed by calcination to decompose the ammonium moiety thereby converting the material to the hydrogen ion-exchanged form.

In the preparation of hydrogen ion-exchanged layered clays we have found that there are disadvantages associated with the aforesaid technique (ii) arising from the use of elevated temperatures in the calcination step. The use of too low a temperature risks incomplete decomposition of the ammonium moiety resulting in a clay containing both ammonium and hydrogen ions. The catalytic activity of the clay so-produced tends to diminish as the proportion of ammonium ions remaining in the clay increases. On the other hand, the use of too high a calcination temperature tends to collapse the lamellar structure and produce an inactive catalyst.

Accordingly, it is preferred to produce a hydrogen ion-exchanged layered clay for use in the process of the present invention by contacting the clay containing exchangeable cations with a solution of an acid under ion-exchange conditions. Preferably the solution of the acid is an aqueous solution. Suitable acids are mineral acids, including sulphuric acid and hydrochloric acid, but other acids, such as carboxylic acids, may be used if so desired. The acid may suitably be from 0.5 to 10 molar. Although contact of the clay with the mineral acid is preferably effected at or near ambient temperature, elevated temperatures which do not destroy the layered structure and the catalytic activity of the clay may be employed, eg up to about 35° C. The period of contact will depend to some extent on the temperature. Typically, at ambient temperature the contact period may be in the range ½ hour to 3 days.

Techniques for separating the fully exchanged clay from the ion-exchange media and excess ions are well known. Any suitable solid/liquid separation procedure can be used. Decantation or centrifugation are two preferred methods for solid/liquid separation. After exchange it is preferred to wash the exchanged clay until all extraneous acid and cations are removed. Thereafter the clay is preferably dried. Although drying is preferably effected at elevated temperature, temperatures which cause collapse of the lamellar structure should be avoided. Generally, drying temperatures in the range 20° to 100° C. are suitable. It is preferred to activate the hydrogen ion-exchanged clay before use as a catalyst by heating in air at a temperature which does not collapse the layered structure, suitably up to 180° C., preferably from 80° to 150° C. The catalyst may suitably be combined with other compounds, for example silica, in order to aid pellet or particle stability.

Hydrogen ion-exchanged layered clays may be used as catalysts in all organic reactions which are catalysed by protons. Advantages arising from their use are that they can be readily separated from the reaction mixture which renders them useful in continuous processes, and they are less corrosive than the conventionally employed strong acids and acid activated clays which also contain free mineral acids. We have found the clays to be particularly useful catalysts in certain specific organic reactions, such as the production of esters by the reaction of an olefin or an olefin oxide with a carboxylic acid, the production of ethers by reaction of an alcohol and an olefin or an olefin oxide, the production of ethers by the reaction of a primary or secondary aliphatic alcohol or an olefin oxide, the production of bis-sec-alkyl ethers from alkenes, the production of alkyl aromatic compounds by the reaction of an aromatic hydrocarbon and an olefin or alcohol and the production of alcohols by the hydration of olefins.

In a particular aspect therefore, the present invention provides a process for the production of an ester which process comprises reacting either an olefin or an olefin oxide with a carboxylic acid in the presence as catalyst of a hydrogen ion-exchanged layered clay under reaction conditions which result in the formation of an ester.

With regard to the olefin or olefin oxide reactant any suitable olefin or olefin oxide may be employed. Suitable olefins include ethylene, propylene, butenes, pentenes and hexenes, diolefins such as butadiene and cyclic olefins such as cyclohexene. Mixtures of olefins such as those commonly encountered in petroleum refinery streams such as those obtained from the steam cracking of hydrocarbons, e.g. catcracked spirit, may also be used if so desired. Suitable olefin oxides include ethylene oxide and propylene oxide. The amount of olefin or olefin oxide employed may be greater or less than the stoichiometric amount required to react completely with the acid.

Both aromatic and aliphatic carboxylic acids may be used. Suitable aliphatic acids include formic, acetic, propionic and butyric acids. Of the aromatic acids phthalic acids, especially orthophthalic acid, may be employed. Mixtures of acids may also be employed if so desired.

Preferably the olefin is ethylene, the carboxylic acid is acetic acid and the ester produced is ethyl acetate. Ethylene glycol diacetate and 2-hydroxyethyl acetate can be obtained from the reaction of ethylene oxide and acetic acid.

The process may be carried out in the liquid phase or in the vapour phase, preferably in the liquid phase. Reaction conditions which result in the formation of an ester will depend on whether the process is carried out in the liquid or the vapour phase and to some extent on the nature of the reactants.

In the liquid phase the pressure is suitably any pressure which maintains a liquid phase at the reaction temperature. In the case of olefins and olefin oxides with suitably high boiling points, e.g. hexene-1, the reaction may for example be conveniently carried out at the reflux temperature of the reactants and under atmospheric pressure, or at higher temperatures and pressures if so desired. The temperature may suitably be in the range 20° to 300° C. In the case of ethylene, for example, the temperature may be in the range 100° to 300° C., preferably 150° to 250° C. Generally, using olefin oxides lower temperatures within the aforesaid range may be employed. In the case of propylene oxide, for example, the temperature may suitably be in the range 20° to 150° C., preferably 50° to 150° C. Solvents may be employed if desired. Suitable solvents include hydrocarbons, e.g. alkanes such as hexane and octane.

In the vapour phase the conditions must be chosen so that the reactants do not liquefy; for example in the production of ethyl-acetate from ethylene and acetic acid, the acetic acid must be fed at atmospheric or slightly higher pressure otherwise it would liquefy at higher pressures. Generally, any temperature which does not result in breakdown of the layered structure of the clay may be employed. In the case of the reaction of ethylene and acetic acid, for example, the temperature may suitably be in the range 120° to 250° C., preferably 140° to 180° C. For the reaction of ethylene and acetic acid the residence time which is defined as:

$$\frac{\text{Volume of catalyst in mls}}{\text{Vapour flow rate (in mls/sec at } NTP)}$$

may suitably be in the range 10 to 60 secs, preferably 20 to 40 secs.

The process may be carried out batchwise or continuously, preferably continuously. The batchwise liquid phase production of ethyl acetate, for example, may conveniently be carried out by charging acetic acid and catalyst to an autoclave, pressurising the autoclave with ethylene, heating the autoclave to the desired reaction temperature and maintaining the autoclave at the reaction temperature. The reaction time should not be unduly protracted otherwise the selectivity for the conversion of acetic acid to ethyl acetate may be adversely affected. Thus at an approximately 2:1 molar ratio of ethylene to acetic acid, an initial ethylene pressure of 55 bar and a temperature of 200° C., the reaction time should preferably not exceed 5 hours. At the completion of the reaction the catalyst may be separated from the product, suitably by filtration, centrifugation or decantation and the reaction product worked up in known manner to recover ethyl acetate therefrom. The catalyst may thereafter be re-used in a further batch reaction with or without intervening treatment.

The invention also provides a process for the production of an ether which process comprises reacting an alcohol with either an olefin or an olefin oxide under reaction conditions which result in the formation of an ether in the presence of a hydrogen ion-exchanged layered clay as catalyst.

Suitably, the alcohol may be an aliphatic, cycloaliphatic or aromatic alcohol, which may be mono-, di- or polyhydric. Examples of suitable aliphatic alcohols include methanol, ethanol, propanols, butanols, pentanols and hexanols. An example of a suitable cycloaliphatic alcohol is cyclohexanol and an example of an aryl alcohol is phenol. Diols, such as ethylene glycol and propylene glycol and polyols, such as glycerol may be used. Mixtures of alcohols and/or diols may be employed if desired.

With regard to the olefin or olefin oxide any suitable olefin or olefin oxide may be employed. Suitable olefins include ethylene, propylene, butenes, pentenes and hexenes, diolefins such as butadiene and pentadiene and cyclic olefins such as cyclohexene and cyclopentadiene. Preferably the olefin is a $C_3$ to $C_6$ linear or branched olefin. Mixtures of olefins such as those commonly obtained from refinery streams, such as those derived from the steam cracking of hydrocarbons, eg cat-cracked spirit, may also be used if so desired. Suitable olefin oxides include ethylene oxide and propylene oxide. The amount of olefin or olefin oxide employed may be greater or less than the stoichiometric amount required to react completely with the alcohol. Generally, using an olefin oxide, it is preferred to employ a stoichiometric excess of the alcohol in order to maximise the yield of desired ether. Preferably the excess of alcohol to olefin oxide is from 5:1 to 15:1 (molar).

In preferred embodiments of the invention mono-, di- or tri-ethylene glycol mono alcohol ethers, where alkyl=methyl, ethyl or butyl, are produced by reacting ethylene oxide with methanol, ethanol or butanol respectively; mono-, di- and tri-propylene glycol monoalkyl ethers are produced by reacting propylene oxide with an alkanol; methyl tertiary butyl ether is produced by reacting methanol with isobutene and 2-methoxybutane is produced by reacting methanol with linear butenes.

The process may be carried out in the liquid phase or in the vapour phase, preferably in the liquid phase. Reaction conditions which result in the formation of an ether will depend on whether the process is carried out in the liquid or the vapour phase and to some extent on the nature of the reactants.

In the liquid phase the pressure is suitably that pressure which maintains a liquid phase at the reaction temperature. In the case of olefins and olefin oxides with suitably high boiling points, e.g. hexene-1, the reaction may for example be conveniently carried out at the reflux temperature of the reactants and under atmospheric pressure, or at higher temperatures and pressures if so desired. Generally, for olefins the temperature may be up to 300° C., preferably 50° to 250° C. The particular temperature employed within the aforesaid ranges will depend upon the nature of the olefin. For example the temperatures employed for linear olefins will be higher than those employed for the corresponding branched olefins. Using alkylene oxides it is preferred to employ generally lower temperatures, which may suitably be in the range from room temperature to 200° C., preferably from 20° to 160° C.

Solvents may be employed if so desired. Suitable solvents include hydrocarbons, e.g. alkanes such as hexane and octane. A preferred solvent is sulpholane.

The process may be carried out batchwise or continuously, preferably continuously.

The invention also provides a process for the production of ethers by reacting at elevated temperature a primary or secondary aliphatic alcohol or a polyol in the presence of a hydrogen ion-exchanged layered clay.

With regard to the primary aliphatic alcohol reactant suitable alcohols include methanol, ethanol, propan-1-ol, butan-1-ol, pentan-1-ol, hexan-1-ol, heptan-1-ol and octan-1-ol. The principal ether in the product resulting from the reaction of a primary aliphatic alcohol in the presence of the lamellar clays is the corresponding 1,1-ether, though the corresponding 1,2-ether, may also be formed. Alkenes and alkene dimers may also be formed. Generally the proportion of alkene in the product increases as the carbon number of the reactant alcohol increases.

With regard to the secondary aliphatic alcohol reactant suitable alcohols include straight-chain alcohols such as propan-2-ol, butan-2-ol, pentan-2-ol, pentan-3-ol, hexan-2-ol and hexan-3-ol and cyclohexanol, of which propan-2-ol and butan-2-ol are preferred. The ethers predominating in the product resulting from the reaction of alkan-2-ol and alkan-3-ols are the 2,2- and 3,3- ethers respectively. Alkenes and alkene dimers are also formed.

The reactant may also be a polyol such as an alkylene glycol. A suitable alkylene glycol is ethylene glycol which produces a mixture of dioxan, and ethylene glycol oligomers (di-ethylene glycol etc). A preferred alkylene glycol is diethylene glycol which produces dioxan in high conversions in the presence of the lamellar clay. Additionally mixtures of alcohols and/or polyols may be used if so desired.

The elevated temperature may suitably be in the range 50° to 300° C., preferably from 150° to 225° C. The process may be carried out in the liquid phase or in the vapour phase, preferably in the liquid phase.

The invention also provides a process for the production of ethers by reacting an olefin oxide at elevated temperature in the presence of a hydrogen ion-exchanged layered clay as catalyst.

Suitable olefin oxides which may be used include ethylene oxide and propylene oxide. Thus, for example, reaction of ethylene oxide yields 1,4-dioxan and 2-methyl-1,3dioxan and the products from the reaction of propylene oxide include 2,5-dimethyl-1,3-dioxan. Other epoxides yield cyclic ethers, but alpha,beta-unsaturated aldehydes may also be formed. The proportion of unsaturated aldehyde generally tends to increase with the carbon number of the epoxide.

The process may be carried out in the liquid phase or the vapour phase, preferably in the liquid phase. The temperature may suitably be in the range 15° to 200° C., preferably 80° to 200° C.

The invention also provides a process for the production of a bis-sec-alkyl ether by reacting an alkene at elevated temperature with intercalated water contained within a hydrogen ion-exchanged layered clay catalyst.

The conditions under which the reaction may be carried out are described in the aforesaid paper by Adams et al in the Journal of Catalysis 58, 238-252 (1979), which is incorporated herein by reference.

The invention also provides a process for the production of an alkyl aromatic compound by reacting at elevated temperature an aromatic hydrocarbon with an alkylating agent selected from olefins and $C_2$ or higher alcohols in the presence as catalyst of a hydrogen ion-exchanged layered clay.

The aromatic hydrocarbon may suitably be benzene, naphthalene or other polycyclic aromatic hydrocarbon. Aromatic hydrocarbons substituted by alkyl or other functional groups, such as for example, hydroxyl, alkoxy and hydroxyalkyl, may also be employed. Preferably the aromatic hydrocarbon is benzene or toluene. Mixtures of aromatic hydrocarbons may also be employed if so desired.

The olefin may suitably be a mono-olefin or a diolefin. Suitable mono-olefins include ethylene, propylene and butylenes, though higher olefins, such as for example propylene tetramer, may be employed. Mixtures of olefins may also be employed. A suitable diolefin is butadiene.

Examples of suitable $C_2$ or higher alcohols which may be employed include ethanol, n-propanol and isopropanol.

In a preferred embodiment of this aspect of the invention benzene is reacted with propylene to produce isopropylbenzene (cumene). In another preferred embodiment benzene is reacted with ethylene to produce ethylbenzene. In a further preferred embodiment phenol is reacted with an alkylating agent to produce alkylphenols.

Reaction of an aromatic hydrocarbon with an alkylating agent may suitably be affected in the liquid phase or in the vapour phase, preferably in the liquid phase. Generally, reaction of an aromatic hydrocarbon with an olefin may be carried out in the liquid phase at a temperature up to 400° C., preferably in the range 150° to 300° C. and at an elevated pressure sufficient to maintain a liquid phase.

The process may be operated batchwise or continuously, preferably continuously.

Typically, under continuous flow conditions, benzene may be alkylated with isopropylene at a temperature in the range from 100° to 400° C., preferably from 150° to 300° C., at atmospheric or elevated pressure, preferably from 20 to 50 bar. The molar ratio of benzene to propylene may be in the range from about 0.1:1 to 100:1, preferably from 3:1 to 15:1. The hydrogen ion-exchanged clay may be any suitable size or shape as to ensure good contact with the reactants. Suitably, particles or pellets may be employed. The ratio of catalyst volume to the liquid feed volume flow rate (residence time) may be up to 5 hours and is preferably in the range from 1 minute to 2 hours. The conditions may be permutated either to maximise desirable products such as cumene or diisopropylbenzene or to minimise any unwanted by-products.

Typically, phenol may be alkylated at a temperature in the range from 50° to 300° C., preferably from 100° to 200° C., at atmospheric or elevated pressure. For example, phenol may be alkylated with high boiling olefins, e.g. hexene-1, at atmospheric pressure and at about 120° C. in a stirred glass vessel fitted with a reflux condenser. Using lower boiling olefins, e.g ethylene and propylene, as the alkylating agent, elevated pressures may be employed to facilitate contact between the phenol and olefin reactants. Alternatively, there may be used other methods of mixing whereby the use of elevated pressure can be avoided, for example by bubbling the olefin through molten phenol containing the catalyst.

The invention also provides a process for the production of an alcohol which process comprises reacting an olefin with water at elevated temperature and pressure in the presence as catalyst of a hydrogen ion-exchanged layered clay.

Suitably the olefin may be a lower olefin such as ethylene, propylene or a butylene, though higher olefins and mixtures of olefins may be employed if desired. Mixtures of olefins also comprise hydrocarbon fractions which contain substantial amounts, eg about 25 to about 90% by weight of olefins. Preferably the olefin is ethylene and the product produced by reaction with water in the presence of the catalyst is ethanol. In another preferred embodiment sec-butanol is produced by reacting linear butenes with water.

In conducting the process of the invention the olefin and water or steam may suitably be passed over the catalyst together at a reactant feed rate corresponding to a space velocity based on liquid reactants in the range of about 0.25 to 10 volumes of liquid feed per volume of catalyst per hour, ie about 0.25 to 10 L.H.S.V. The water to olefin mole ratio may be in the range of about 1:1 to 500:1 preferably from 5:1 to 400:1.

The total pressure in the reactor may range from about 50 psig to about 1500 psig and the temperature may be in the range from 50° to 400° C. The specific temperature chosen depends on the reactivity of the olefin. Thus, propylene and the butenes are considerably more reactive than ethylene, and for the former olefins a temperature in the range of about 100° to about 240° C. is suitable. For ethylene the temperature may suitably be in the range from about 200° to 400° C. Since low temperatures are associated with high values of the equilibrium constant for alcohol formation, it is desirable to hydrate at the lowest temperature compatible with a reasonable rate of conversion.

The liquid phase reaction may be carried out in the presence of a solvent. A suitable solvent, for example, is ethyl carbitol.

The process may suitably be conducted in what is conventionally known as a "trickle bed" reactor, with at least a portion of the water in the liquid phase. Alternatively, the process may be operated in the gas phase.

The invention will now be illustrated by reference to the following Examples.

All analytical results were determined using gas chromatography and the identity of the products was confirmed by comparison with authentic materials, mass spectroscopy or nuclear magnetic resonance spectroscopy. Generally, analyses are expressed by weight but in some Examples flame ionisation gas chromatographic areas are used to express the results.

PREPARATION OF HYDROGEN ION-EXCHANGED LAYERED CLAY

EXAMPLE 1

Sodium bentonite (a Wyoming Bentonite supplied as a fine powder for use in drilling muds) was added to a solution of concentrated sulphuric acid (400 ml) in water (1100 ml) and left at room temperature for 2 days with occasional stirring. The clay was separated from the solution and washed with water by repeated centrifuging and resuspending in water until the pH of the supernatant solution was the same as the distilled water used in the washing. The clay was dried at 80° C. in air and ground to give a fine powder of hydrogen bentonite.

Hydrogen ion-exchanged bentonites prepared in the aforesaid manner were used in all the subsequent Examples.

PRODUCTION OF ESTERS BY REACTING AN OLEFIN OR OLEFIN OXIDE WITH A CARBOXYLIC ACID

(A) IN THE VAPOUR PHASE

EXAMPLE 2

Granules of hydrogen bentonite were packed in the lower portion of a glass reactor tube. A 2:1 molar ratio mixture of ethylene and acetic acid was passed over the catalyst which was maintained at 170° to 180° C. and ambient pressure, the residence time being 30 seconds. The effluent vapours were condensed to give a liquid product containing 22.4% w/w ethyl acetate which had been produced from acetic acid with greater than 99% selectivity.

(B) IN THE LIQUID PHASE

EXAMPLE 3

10 g of hydrogen bentonite and acetic acid (80 g) were added to a Baskerville 100 ml stainless steel autoclave fitted with a stirrer. The autoclave was pressurised with ethylene (approximately 2:1 molar ratio of ethylene to acetic acid) so that the required pressure (55 bar) was reached at the reaction temperature (200° C.). The autoclave was kept at 200° C. for 2.5 hours and then cooled. The liquid products were shown to contain 39.8% ethyl acetate formed from acetic acid with greater than 99% selectivity.

EXAMPLE 4

Hydrogen ion-exchanged bentonite (0.5 g) which had previously been equilibrated in a dessicator over granular anhydrous calcium chloride, hex-1-ene (5 ml) and acetic acid (1.5 ml) were placed in a standard steel reactor of capacity 20 ml. The reactor was closed by a screw cap provided with an O-ring seal and immersed up to the screw cap in a silicone oil bath which was maintained at 200° C. After 4 hours the reactor was removed from the bath, cooled and its contents analysed. The results in terms of the weight percentage of the individual products (rounded to the nearest whole number) are given in Table 1.

EXAMPLE 5

Example 4 was repeated except that acetic acid was replaced by propionic acid.

EXAMPLE 6

Example 4 was repeated except that acetic acid was replaced by isobutyric acid.

EXAMPLE 7

Example 4 was repeated except that hex-1-ene was replaced by hept-1-ene.

EXAMPLE 8

Example 4 was repeated except that hex-1-ene was replaced by oct-1-ene.

EXAMPLE 9

Example 4 was repeated except that hex-1-ene was replaced by 4-methylpent-1-ene.

EXAMPLE 10

Example 4 was repeated except that hex-1-ene was replaced by hex-2-ene.

The results of Example 4 to 10 are given in Table 1.

TABLE 1

| Ex. | Alkene | Acid | Weight % of product mixture | | | |
|---|---|---|---|---|---|---|
| | | | alkene | acid | total esters | alkene dimers |
| 4 | Hex-1-ene | acetic | 44 | 40 | 14 | 3 |
| 5 | Hex-1-ene | propionic | 41 | 30 | 10 | 19 |
| 6 | Hex-1-ene | isobutyric | 34 | 35 | 10 | 21 |
| 7 | Hept-1-ene | acetic | 55 | 35 | 8 | 2 |
| 8 | Oct-1-ene | acetic | 62 | 23 | 13 | 2 |
| 9 | 4 Mepent-1-ene | acetic | 52 | 31 | 9 | 9 |
| 10 | Hex-2-ene | acetic | 54 | 24 | 18 | 4 |

EXAMPLE 11

Example 4 was repeated except that hex-1-ene was replaced by 1,5-hexadiene. The product contained 5% ester and 7% alkene dimers.

EXAMPLE 12

Example 4 was repeated except that hex-1-ene was replaced by cyclohexene. 15% of new products were obtained, 10% being ester.

EXAMPLE 13

Hydrogen ion-exchanged bentonite (1.5 g) was added to acetic acid (16.5 g) in an 100 ml flask equipped with a cardice/acetone condenser and the mixture stirred at 60° C. Propylene oxide (16 g) was added dropwise over a period of about 4 hours and after a further 30 minutes the reaction mixture was analysed. This showed the product to contain propylene glycol mono-acetate (about 33%), di-methyldioxans (about 20%), unreacted acetic acid and propylene oxide.

PRODUCTION OF ETHERS BY REACTING AN ALCOHOL WITH AN OLEFIN OR OLEFIN OXIDE

EXAMPLE 14

The procedure described in Example 4 was followed except that the hex-1-ene and acetic acid were replaced by a 50:50 v/v mixture (5 ml) of hexan-1-ol and hex-1-ene. The analysis of the product mixture gave:

| | wt % of product mixture |
|---|---|
| Hexenes | 46 |
| Hexanol | 10 |
| 1,1-ether | 18 |
| 1,2- and 1,3-ethers | 8 |
| alkene dimers | 18 |

EXAMPLE 15

5 g of hydrogen ion-exchanged bentonite, hex-1-ene (25 g) and methanol (19 g) were sealed in a Baskerville 100 ml stainless steel autoclave fitted with a stirrer. The autoclave was heated at 150° C. for 2.5 hours, then cooled. The liquid products (37.5 g, 85% weight recovered) were recovered and shown to contain 2-methoxyhexane (19%) and dimethyl ether (7%) as the two major products. The product percentages are based on peak areas shown in a flame ionisation gas chromatograph. The gaseous products were not examined.

EXAMPLE 16

As Example 15 but using ethanol (19 g) instead of methanol. The sealed autoclave was pressurised with nitrogen to give a reaction pressure of 50 bar at 180° C. The autoclave was heated at 180° C. for 2.5. hours, and then cooled. The liquid products (35.1 g, 80% weight recovered) were recovered and shown to contain 2-ethoxyhexane (23.5%) and diethyl ether (8.8%) as the two major products. The product percentages are based on peak areas shown on a flame ionisation gas chromatograph. The gaseous products were not examined.

EXAMPLE 17

5 g of hydrogen ion-exchanged bentonite and methanol (19 g) were cooled to −20° C. in the detached bottom-half of a Baskerville 100 ml stainless steel autoclave. But-1-ene (ca 30 ml of condensed liquid in a card-ice cold trap) was added and the autoclave sealed. The autoclave was flushed with nitrogen and stirred at 200° C. for 2.5 hours, and allowed to cool. The liquid products (7 g, 18% weight recovered) were recovered and shown to contain 2-methoxybutane (40%) and dimethyl ether (55%) and a little $C_4$ dimers as the major products. The product percentages are based on peak areas shown on a flame ionisation gas chromatograph. The gaseous products were not examined.

EXAMPLE 18

Hydrogen ion-exchanged bentonite (3.75 g) and ethylene glycol (30 g) were sealed in a 100 ml stirred autoclave which was charged with liquid propane (40 ml). The autoclave was heated at 175° C. for 2.5 hours where a maximum pressure of 35 bar was reached. After cooing and venting the liquid products were analysed and the results are shown in Table 2.

EXAMPLE 19

Example 18 was repeated except that sulpholane (20 g) was added as solvent and 20 g of ethylene glycol was used instead of 30 g. The results are shown in Table 2.

TABLE 2

| | % w/w in liquid product | | | |
|---|---|---|---|---|
| Example | Isopropyl cellosolve | Dioxan | Digol | Propanol |
| 18 | 19.9 | 1.0 | 9.9 | 0.7 |
| 19* | 46.8 | 0.4 | 2.8 | 2.8 |

*excluding sulpholane solvent

EXAMPLE 20

Example 18 was repeated except that but-1-ene (40 ml) was used instead of propene. The results are shown in Table 3.

EXAMPLE 21

Example 19 was repeated except that but-1-ene (40 ml) was used instead of propane. The results are shown in Table 3.

TABLE 3

| | % w/w in products | | |
|---|---|---|---|
| Example | sec-butyl cellosolve | Dioxan | Digol |
| 20 | 7.9 | 1.7 | 5.8 |
| 21* | 27.0 | 0.5 | 3.3 |

*excluding sulpholane solvent

EXAMPLE 22

Into a 200 ml stirred stainless steel autoclave was placed methanol (19 g, 0.59 mole) and hydrogen ion-exchanged bentonite. The autoclave was sealed and charged with liquid isobutene (approximately 40 ml, 0.5 mole) and then stirred at 80° C. for 2 hours. The maximum pressure obtained was 15 bar. After reaction, the autoclave was allowed to cool and any gaseous products were vented off. The liquid products recovered (46.0 g) contained 80% by weight of methyl tertiarybutyl ether made in a yield of approximately 84% from isobutene.

EXAMPLE 23

Hydrogen ion-exchanged bentonite (1 g) was added to a stirred solution of ethylene oxide (10 g) in ethanol (25 ml) at room temperature in a flask equipped with a dry ice/acetone condenser. A virtually complete conversion of ethylene oxide was obtained within 30 minutes and the product contained mono-ethylene glycol mono-ethyl ether and diethylene glycol mono-ethyl ether (about 3:1 ratio by weight) and unreacted ethanol.

Comparison Test

A solution of ethylene oxide (10 g) in ethanol (25 ml) was stirred for 30 minutes at room temperature in a flask equipped with a dry ice/acetone condenser. No ethylene glycol ether products were detected by gas chromatographic analysis.

EXAMPLE 24

Hydrogen ion-exchanged bentonite (1.5 g) was added to ethanol (100 g; 2.17 mole) in a flask equipped with a dry ice/acetone condenser. Propylene oxide (13.2 g; 0.23 mole) was added dropwise to the reaction mixture which was stirred at room temperature. Analysis of the product after a few minutes showed virtually quantitative conversion of the propylene oxide to mono-propylene glycol mono-ethyl ether and di-propylene glycol mono-ethyl ether (about 9:1 ratio by weight).

EXAMPLE 25

Example 24 was repeated except that the propylene oxide was replaced by ethylene oxide (14 g; 0.23 mole) and the amount of ethanol (123 g; 2.8 mole) increased. Analysis of the product showed virtually quantitative conversion of the ethylene oxide to mono-ethylene glycol mono ethyl ether and di-ethylene glycol mono ethyl ether (about 9:1 ratio by weight).

EXAMPLE 26

Hydrogen ion-exchanged bentonite (1.5 g) was added to n-butanol (22 g; 0.33 mole) in a flask equipped with a dry ice/acetone condenser. Ethylene oxide (13.2 g; 0.30 mole) was added dropwise and analysis of the product after a few minutes showed the product distribution, as measured from gas chromatography areas, to be ethylene glycol mono-butyl ether (45%), diethylene glycol mono-butyl ether (40%), unreacted butanol (5%) and ethylene oxide (10%).

PRODUCTION OF ETHERS BY REACTING A PRIMARY OR SECONDARY ALIPHATIC ALCOHOL OR A POLYOL IN THE PRESENCE OF A HYDROGEN ION-EXCHANGED LAYERED CLAY

EXAMPLE 27

Hydrogen ion-exchanged bentonite (0.5 g) which had previously been equilibrated in a desiccator over calcium chloride and propan-2-ol (5 ml) were placed in a standard steel reactor of capacity 20 ml. The reactor was closed by a screw cap provided with an O-ring seal and immersed up to the screw cap in a silicone oil bath which was maintained at 200° C. After 4 hours the reactor was removed from the bath, cooled and its contents analysed. The results in terms of wt. % of individual products in the product mixture are in the following Table 4.

EXAMPLE 28

Example 27 was repeated except that butan-2-ol was used in place of propan-2-ol.

EXAMPLE 29

Example 27 was repeated except that pentan-2-ol was used in place of propan-2-ol.

EXAMPLE 30

Example 27 was repeated except that hexan-2-ol was used in place of propan-2-ol.

EXAMPLE 31

Example 27 was repeated except that butan-1-ol was used in place of propan-2-ol.

EXAMPLE 32

Example 27 was repeated except that pentan-1-ol was used in place of propan-2-ol.

EXAMPLE 33

Example 27 was repeated except that hexan-1-ol was used in place of propan-2-ol.

EXAMPLE 34

Example 27 was repeated except that heptan-1-ol was used in place of propan-2-ol.

EXAMPLE 35

Example 27 was repeated except that octan-1-ol was used in place of propan-2-ol.

EXAMPLE 36

Example 27 was repeated except that 3-methylbutan-1-ol was used in place of propan-2-ol.

EXAMPLE 37

Example 27 was repeated except that 3-methylpentan-1-ol was used in place of propan-2-ol.

The results of Examples 27 to 37 are given in Table 4.

EXAMPLE 38

Example 27 was repeated except that diethylene glycol was used in place of propan-2-ol. Analysis of the product showed:

|  | wt % reaction mixture |
| --- | --- |
| Unreacted glycol | 36 |
| Dioxan | 31 |
| Ethylene glycol | 9 |
| Triethylene glycol | 20 |
| Others | 4 |

TABLE 4

| | | Weight % of reaction product | | | | | |
| --- | --- | --- | --- | --- | --- | --- | --- |
| Example | Alkanol | Unreacted alkanol | 2,2 dialkyl ether | 1,1 dialkyl ether | 1,2 dialkyl ether | Alkenes | Alkene dimers |
| 27 | Propan-2-ol | 46 | 48 | — | — | 5* | 1 |
| 28 | Butan-2-ol | 25 | 43 | — | — | 28* | 4 |
| 29 | Pentan-2-ol | 9 | 2 | — | — | 82 | 3 |
| 30 | Hexan-2-ol | 8 | 4 | — | — | 86 | 1 |
| 31 | Butan-1-ol | 27 | — | 53 | 6 | 12* | 1 |
| 32 | Pentan-1-ol | 40 | — | 40 | 4 | 9 | 7 |
| 33 | Hexan-1-ol | 33 | — | 48 | 4 | 12 | 3 |
| 34 | Heptan-1-ol | 31 | — | 50 | 2 | 14 | 4 |
| 35 | Octan-1-ol | 43 | — | 40 | — | 13 | 4 |
| 36 | 3-Methyl butan-1-ol | 40 | — | 45 | — | 4 | 10 |
| 37 | 3-Methyl pentan-1-ol | 43 | — | 31 | — | 12 | 15 |

*Due to loss of gaseous alkenes on sampling these figures are much too small - hence all others in the relevent lines are maxima.

PRODUCTION OF AN ALCOHOL BY REACTING AN OLEFIN WITH WATER IN THE PRESENCE OF A HYDROGEN ION-EXCHANGED LAYERED CLAY

EXAMPLE 39

Hydrogen ion-exchanged bentonite (3.75 g) and water (40 g) were sealed in a 100 ml stirred autoclave which was then charged with 40 ml liquid butene-1. The autoclave was heated to 200° C. for 2.5 hours giving a maximum pressure of 65 bar. After cooling and venting 38.7 g of liquid product having the butan-2-ol content shown in Table 5 was obtained.

EXAMPLE 40

Example 39 was repeated except that ethyl carbitol (20 g) was added as solvent and the amount of water was reduced from 40 g to 20 g. The results are given in Table 5.

TABLE 5

| Example | Yield of butan-2-ol in liquid product (g) | Conversion of but-1-ene to butan-2-ol (%) |
|---|---|---|
| 39 | 1.55 | 4.2 |
| 40 | 2.24* | 6.1 |

*excluding ethyl carbitol solvent

EXAMPLE 41

Water (40 grams per hour) was passed over a bed containing hydrogen ion-exchanged bentonite (20 ml. mesh size 1.4 mm particles) mixed with 20 ml inert diluent in a continuous flow high pressure apparatus charged to 40 bar with ethylene and maintained at 40 bar with a slow ethylene bleed both in and out of the apparatus. At a reaction temperature of 280° C., 0.5% weight of water was converted to ethanol and at 390° C. 0.3% weight of water was converted to ethanol. No other products were observed.

THE PRODUCTION OF AN ALKYL AROMATIC COMPOUND BY REACTING AN AROMATIC HYDROCARBON WITH AN ALKYLATING AGENT

EXAMPLE 42

Into a 200 ml stirred stainless steel autoclave was placed benzene (120 g, 1.52 mole) and hydrogen ion-exchanged bentonite (10 g). The autoclave was sealed and charged with liquid propylene (about 20 ml, 0.25 mole) then stirred (400 rpm) at 230° C. for 2.5 hours. The maximum pressure obtained was 28 bar. After reaction, the autoclave was allowed to cool and any gaseous products were vented off. The liquid products and catalyst were removed to give liquid products (124 g) which contained cumene (19.7% by weight, made in a yield of approximately 81% from propylene) and diisopropyl benzenes (1.5% by weight, made in a yield of approximately 4.5% from propylene) as major products.

EXAMPLE 43

Example 42 was repeated except that the amount of hydrogen ion-exchanged bentonite was reduced from 10 g to 2.5 g. The liquid products (126 g) contained cumene (20.9% by weight) and diisopropyl benzenes (1.5% by weight) made in a yield of approximately 88 and 4.5% from propylene respectively.

EXAMPLE 44

A solution of benzene and isopropylene (about 4:1 mole ratio) was fed over a hydrogen ion-exchanged bentonite catalyst (40 ml) in the reactor of a continuous plant at a rate of 20 ml to 90 ml per hour at a reaction temperature of 230° C. and a pressure maintained at 30 bar. A typical analysis of the liquid products with a feed rate of 90 ml per hour showed 69% benzene, 26% cumene and 5% diisopropyl benzenes by weight.

EXAMPLE 45

Into a 200 ml stirred stainless steel autoclave was placed toluene (70 g, 0.76 mole) and hydrogen ion-exchanged bentonite (5 g). The autoclave was sealed and charged with ethylene to 40 bar. The autoclave was then stirred (400 rpm) at 200° C. for 2.5 hours when a maximum pressure of 65 bar was attained. On cooling and venting of any gaseous products, the liquid products and catalyst were removed. The liquid products (64 g) contained isomers of ethyl toluene (4.6% by weight) in the meta-ortho:para ratio of 1:1.6:1.

EXAMPLE 46

Phenol (9.4 g, 0.1 mole), hex-1-ene (8.4 g, 0.1 mole) and hydrogen ion-exchanged bentonite (1 g) were gently refluxed in a two-necked flask (50 ml) fitted with a condenser and a serum cap through which small samples of reaction product could be periodically removed by syringe. After 30 minutes reaction time, the reaction mixture contained unreacted phenol (6%), isomers of hexyl phenol (67%) and isomers of dihexyl phenol (26%).

We claim:

1. A process for the production of an alkyl aromatic compound by reacting at elevated temperature an aromatic hydrocarbon with an alkylating agent selected from olefins and $C_2$ or higher alcohols in the presence of a hydrogen ion-exchanged layered clay catalyst.

2. A process according to claim 1 wherein said alkylating agent is a $C_2$ or higher alcohol.

3. A process according to claim 1 wherein said alkylating agent is an olefin.

4. A process according to claim 1 wherein the aromatic hydrocarbon is either benzene or toluene.

5. A process according to claim 1 wherein the olefin is a mono-olefin selected from ethylene, propylene and the butylenes.

6. A process according to claim 1 wherein the $C_2$ or higher alcohol is ethanol, n-propanol or isopropanol.

7. A process according to claim 1 wherein benzene is reacted with propylene to produce isopropylbenzene.

8. A process according to claim 1 wherein benzene is reacted with ethylene to produce ethylbenzene.

9. A process according to claim 1 wherein an aromatic hydrocarbon is reacted with an olefin in the liquid phase at a temperature in the range 150° to 300° C. and at an elevated pressure sufficient to maintain a liquid phase.

10. A process according to claim 1 wherein benzene is alkylated with propylene under continuous flow conditions at a temperature from 150° to 300° C. and a pressure from 20 to 50 bar.

11. A process according to claim 1 wherein the layered clay is a montmorillonite.

* * * * *